(12) United States Patent
Doerschner et al.

(10) Patent No.: US 10,112,761 B2
(45) Date of Patent: Oct. 30, 2018

(54) PACKAGE HAVING INTEGRAL TAB WITH FINGER HOLE OPENING FEATURE

(71) Applicant: Hollister Incorporated, Libertyville, IL (US)

(72) Inventors: David L. Doerschner, Cary, IL (US); Jerome A. Henry, Castlebar (IE); David Hannon, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 27 days.

(21) Appl. No.: 15/110,698

(22) PCT Filed: Jan. 8, 2015

(86) PCT No.: PCT/US2015/010645
§ 371 (c)(1),
(2) Date: Jul. 8, 2016

(87) PCT Pub. No.: WO2015/105990
PCT Pub. Date: Jul. 16, 2015

(65) Prior Publication Data
US 2016/0325903 A1    Nov. 10, 2016

Related U.S. Application Data

(60) Provisional application No. 61/925,463, filed on Jan. 9, 2014.

(51) Int. Cl.
*B65D 75/58* (2006.01)
*B65D 75/06* (2006.01)
*A61M 25/00* (2006.01)

(52) U.S. Cl.
CPC ....... *B65D 75/5838* (2013.01); *A61M 25/002* (2013.01); *A61M 25/0017* (2013.01); *B65D 75/06* (2013.01); *B65D 75/5833* (2013.01)

(58) Field of Classification Search
CPC .......................... B65D 75/5838; B65D 75/06; B65D 75/5833; A61M 25/0017; A61M 25/002
(Continued)

(56) References Cited

U.S. PATENT DOCUMENTS

| 3,286,832 A | 11/1966 | Pilger |
| 3,291,377 A | 12/1966 | Eggen |

(Continued)

FOREIGN PATENT DOCUMENTS

| DE | 2458462 | 6/1976 |
| DE | 3115144 | 1/1982 |

(Continued)

OTHER PUBLICATIONS

International Search Report and Written Opinion for PCT/US2015/010645 dated Apr. 23, 2015.

*Primary Examiner* — Chun Cheung
(74) *Attorney, Agent, or Firm* — Cook Alex Ltd.

(57) ABSTRACT

A package (10) for an elongated article has a sheet material with side (1, 6), upper (2, 5) and lower (3, 4) panels. The side panels are arranged to confront one another at a fin (20) and are at least partially adhered to one another at a longitudinal fin seal (28). The upper and lower panels extend from the fin to define a package body (12) which receives the elongated article. First and second end portions of the sheet material confront one another and are adhered to one another to form first and second end seals (16, 18) which enclose the interior cavity (14) of the package body. A starter line (36) is formed in the fin and extends from a free edge (24) thereof toward non-sealed portions (32) of the panels (1, 6) of the package.

29 Claims, 3 Drawing Sheets

(58) Field of Classification Search
USPC .......................... 206/364; 383/20, 202, 205
See application file for complete search history.

(56) References Cited

U.S. PATENT DOCUMENTS

| | | | |
|---|---|---|---|
| 3,411,620 A | | 11/1968 | Steinbock |
| 4,658,963 A | | 4/1987 | Jud |
| 4,834,245 A | * | 5/1989 | Ohga ..................... B32B 27/32 383/201 |
| 4,966,286 A | | 10/1990 | Muckenfuhs |
| 5,229,180 A | | 7/1993 | Littmann |
| 5,366,295 A | | 11/1994 | Montesissa et al. |
| 5,409,115 A | * | 4/1995 | Barkhorn ........... B65D 75/5833 206/440 |
| 5,445,454 A | | 8/1995 | Barkhorn |
| 5,836,697 A | | 11/1998 | Chiesa |
| 5,885,673 A | * | 3/1999 | Light ..................... B32B 27/08 206/455 |
| 6,352,364 B1 | * | 3/2002 | Mobs ..................... B65D 75/44 229/87.05 |
| 6,889,483 B2 | | 5/2005 | Compton et al. |
| 7,470,062 B2 | * | 12/2008 | Moteki .................. B65B 61/18 229/87.05 |
| 7,770,726 B2 | * | 8/2010 | Murray ............... A61M 25/002 206/210 |
| 7,770,728 B2 | | 8/2010 | Kaern |
| 7,862,869 B2 | | 1/2011 | Papenfuss et al. |
| 8,690,431 B2 | * | 4/2014 | Hughes ................. B65D 75/44 383/200 |
| 2003/0168375 A1 | * | 9/2003 | Jarvis ..................... B65D 65/40 206/532 |
| 2010/0198195 A1 | | 8/2010 | Nishtala et al. |
| 2011/0266180 A1 | | 11/2011 | Wipf et al. |
| 2012/0310219 A1 | | 12/2012 | Meek et al. |
| 2014/0151260 A1 | * | 6/2014 | Frank ..................... B65D 31/04 206/524.5 |
| 2016/0176601 A1 | * | 6/2016 | Boekeloo .............. B65D 75/12 206/457 |

FOREIGN PATENT DOCUMENTS

| | | |
|---|---|---|
| EP | 0280528 | 8/1988 |
| EP | 1291294 | 3/2003 |
| EP | 2484603 | 8/2012 |
| EP | 2570367 | 3/2013 |
| FR | 2346243 | 10/1977 |
| GB | 1440461 | 6/1976 |
| WO | WO 1996/023711 | 8/1996 |
| WO | WO 1998/006642 | 2/1998 |
| WO | WO 2001/052763 | 7/2001 |
| WO | WO 2007/099129 | 9/2007 |
| WO | WO 2008/104444 | 9/2008 |
| WO | WO 2011/146627 | 11/2011 |
| WO | WO 2012/100996 | 8/2012 |

* cited by examiner

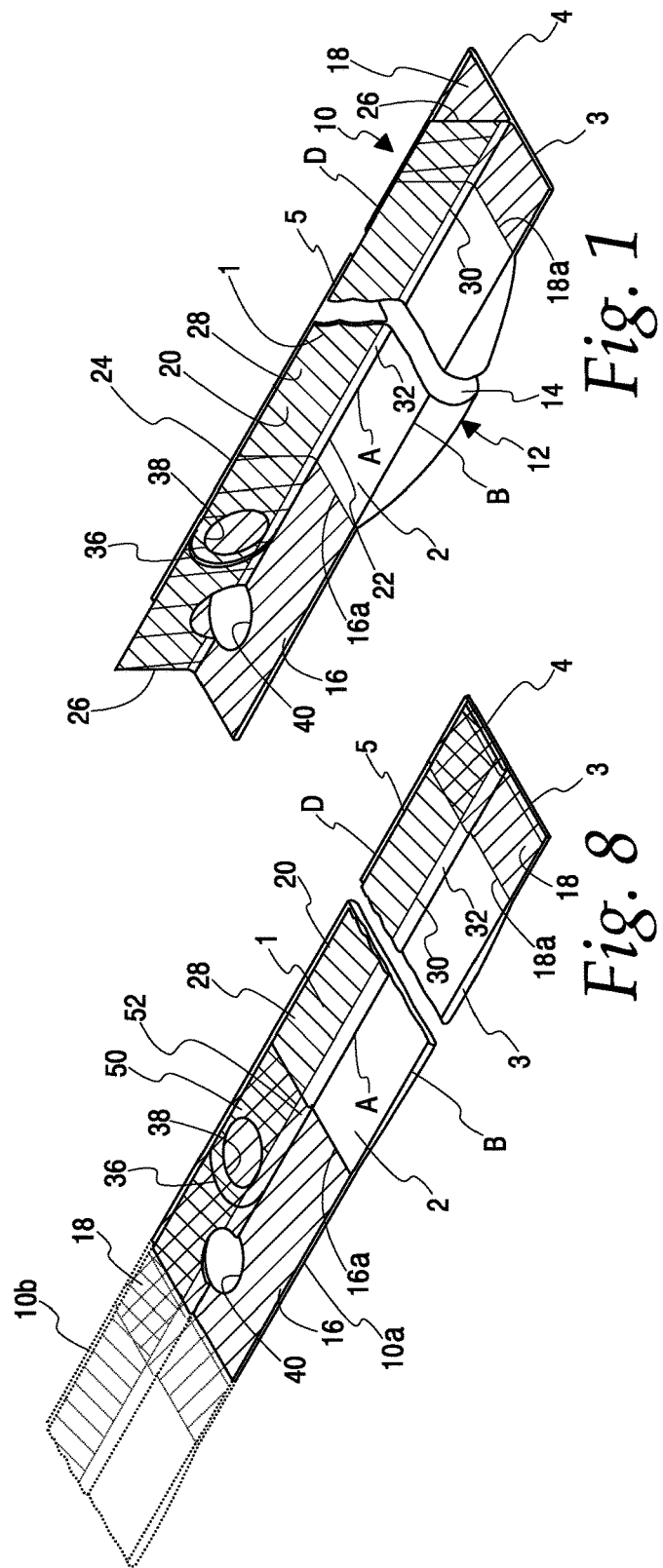

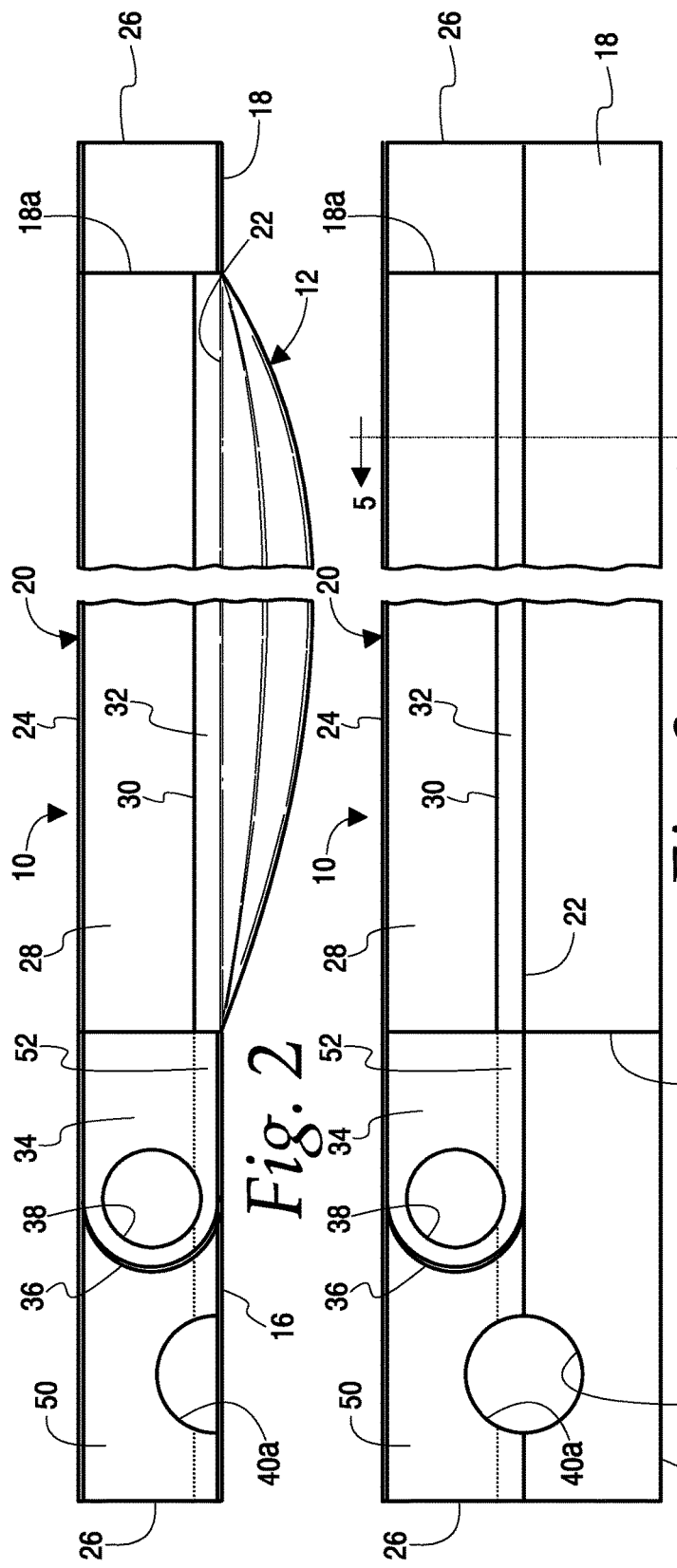
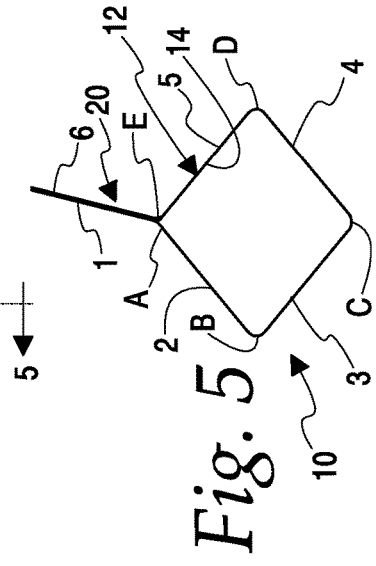

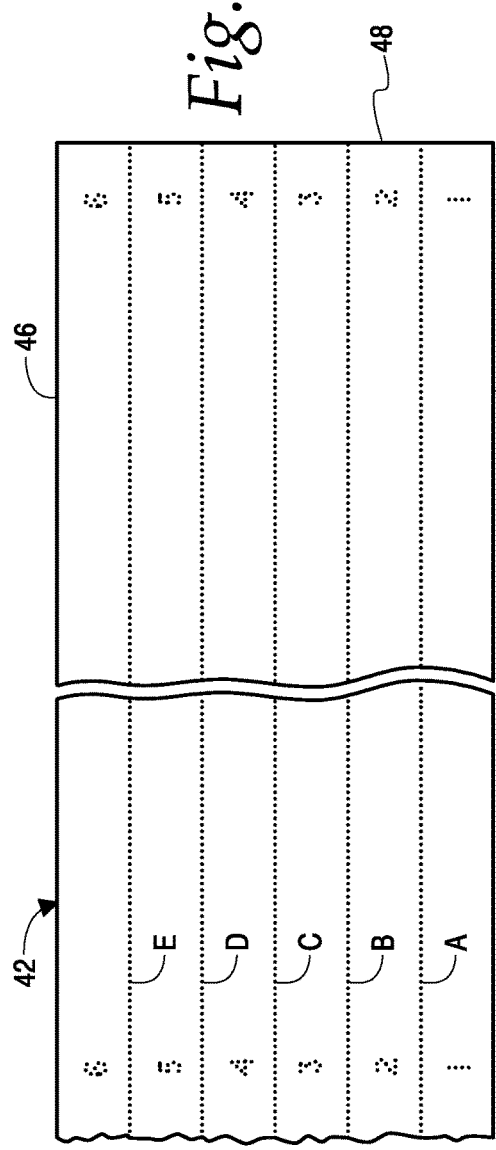
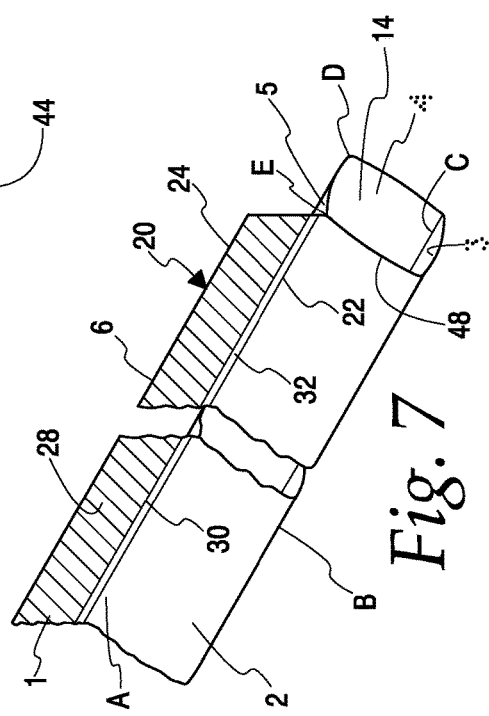

PACKAGE HAVING INTEGRAL TAB WITH FINGER HOLE OPENING FEATURE

RELATED APPLICATION

This application is the U.S. National Stage of PCT International Patent Application No. PCT/US2015/010645, filed Jan. 8, 2015, which claims the benefit of and priority to U.S. Provisional Patent Application Ser. No. 61/925,463, filed Jan. 9, 2014, the contents of which are incorporated by reference herein.

FIELD OF THE DISCLOSURE

The present disclosure is generally related to packaging and more particularly to a package for elongated articles such as catheters.

BACKGROUND

Intermittent catheterization is a good option for many people who suffer from various abnormalities of the urinary system. Those with such abnormalities often find it desirable to use individually-packaged, sterile catheters designed for a single use. An important criteria for such a single use product includes the cost and ease of use in performing intermittent catheterization. With regard to both cost and ease of use, these factors apply to both the catheter itself and the package for the catheter. It is desirable that end users find the package acceptable to enhance the chances of successful intermittent catheterization. In this regard an important factor in catheter package design is recognition that some catheter users will have limited manual dexterity, which can make it difficult for them to open a conventional package.

One type of known catheter package is shown in U.S. Pat. No. 7,770,726. The package in this patent uses a tear strip located inside the package at one edge and running essentially the entire length of the package. The tear strip is anchored at one end to an end seal. A portion of the end seal with the tear strip attached is severable from the package which allows the user to grasp the end seal portion and use it to pull the tear strip down the length of the package. The tear strip severs the material of the body of the package and causes the package to open.

Other catheter packages have been made with directional tear laminates. The problem with these has been the fact that there is an opportunity for the tear line to progress in a non-longitudinal direction with the result that a corner or other portion of the package is removed without completely opening the body of the package.

SUMMARY

In one aspect the present disclosure is directed to a package formed of an elongated sheet material wrapped about a product such as a catheter. The wrapped sheet material forms a package body which defines a cavity for receiving the product. Side panels of the wrapped sheet material are in contact with one another to define a fin. At least a portion of the contacting side panels of the fin may be sealed together to define a fin seal. The fin and fin seal extend along the full length of the package. The fin may be connected to the package body at a fold line. The edges of the fin not at the fold line define a free edge of the fin.

The ends of the package may be closed by first and second end seals. The end seals may be formed by pinching the end portions of the sheet material that are opposite the fin toward the fin until adjacent portions of the sheet material are in contact with one another. These contacting end portions may then be sealed together in a direction transverse to the length of the package.

A pull tab is formed in the fin by a starter line that extends from the free edge of the fin toward the fold line. The starter line can be cut fully through the fin, or it can be a score line that weakens the fin but is not cut fully through, or it can be a perforated line, or a combination of these. In any case the starter line defines a pull tab which can be engaged by a user to enable him or her to pull on the fin and remove at least the fin seal from the majority of the package and thereby open the package. When the fin is used to tear open the package a clean, straight tear is consistently achieved.

A finger hole may be included in the pull tab to promote easy opening of the package. A second finger hole may be included in an end seal.

BRIEF DESCRIPTION OF THE DRAWINGS

FIG. 1 is a perspective view of the package according to the present disclosure, with the fin seal extending out of the plane of the end seals where it is ready for opening the package.

FIG. 2 is a side elevation view of the package according to the present disclosure, with the fin seal terminal line shown schematically in the areas of the end seals by dotted lines.

FIG. 3 is a top plan view of the package with the fin folded down approximately into the plane of the end seals, and with the fin seal terminal line shown schematically in the area of the end seals by dotted lines.

FIG. 4 is an end elevation view of the package with the fin extending upwardly in a substantially natural position.

FIG. 5 is a section taken along line 5-5 of FIG. 3 but with the fin shown moved from the position of FIG. 3 so that the fin extends upwardly in a substantially natural position.

FIG. 6 is top plan view of the end portion of a roll of sheet material used for forming the package, the material being shown lying flat prior to any forming operation.

FIG. 7 is a perspective view of the package after initial forming operations have wrapped the sheet material and formed a fin seal.

FIG. 8 is a perspective view of the package after subsequent forming operations have folded down the fin seal and pinched and sealed the ends to form the end seals.

DETAILED DESCRIPTION OF THE EMBODIMENTS

FIG. 1 shows an embodiment of the package 10 of the present invention. The package may be formed by wrapping an elongated sheet material around a catheter or other elongated product (not shown). The wrapped sheet includes a body 12 which defines a three-dimensional cavity 14 therein for receiving the product. The body 12 joins a first end seal 16 at one end and a second end seal 18 located at the opposite end of the package. The boundaries of the first and second end seals are shown at 16a and 18a, respectively.

A longitudinal fin 20 extends the length of the package. As will be more fully explained below, the fin may be formed by confronting side panels of the wrapped sheet material. The fin 20 is joined to the body 12 and end seals 16, 18 at a fold line 22. The boundaries of the fin not at the fold line 22 define a free edge. In the embodiment shown the fin has both a longitudinal free edge 24 and two end free edges 26. While the end free edges are conveniently made to be perpendicular to the longitudinal free edge as shown, one or both of the end free edges could have a different configuration, such as a curved portion that merges with the longitudinal free edge.

Other views of the package 10 are shown in FIGS. 2-5. At least a portion of the confronting side panels of the fin 20 are held in contact with one another and sealed at a fin seal 28. In the illustrated embodiment the fin seal extends from the longitudinal free edge 24 to a fin seal terminal line shown at 30. Thus, there is preferably a non-sealed portion 32 of the fin between the terminal line 30 and the fold line 22. It will be understood that the fin seal 28 could be located differently on the fin 20. For example, the fin seal could extend fully from the free edge 24 to the fold line 22. Alternatively, the fin seal could extend from the fold line 22 partially toward the free edge 24. In another alternative there could be a longitudinal hiatus in the fin seal, i.e, there could be sealed longitudinal strips both above and below a non-sealed portion. While various arrangements of the fin seal are possible, some portion of the fin must be sealed at all longitudinal points along its length.

A pull tab 34 is formed in the fin 20 by a starter line 36 that extends to one of the free edges of the fin, in this case the longitudinal free edge 24. The starter line as shown at 36 may be a generally semi-circular cut fully through the thickness of the fin 20 and extends to or near the fold line 22 in the area of the first end seal 16. Preferably the starter line will extend to a single-sealed area of the fin, as will be more fully explained below. This means the starter line will approach the fold line 22 to about a quarter inch from the fold line, although it could stop short of that. It may also be preferred that the last portion (e.g., a quarter inch or so) of the internal end of the starter line be directed within 15 to 20 degrees of parallel to the fold line 22, although other arrangements are possible. This will tend to direct the intentional opening tear line along the fold line 22 and fin seal terminal line 30.

It will be noted that the starter line 36 does not extend on to any portion of the end seal 16; only the fin 20 has the starter line. Furthermore, the starter line 36 extends all the way to a free edge 24 or 26 of the fin 20 to facilitate the beginning of an opening tear. While the starter line extends to a fin free edge, it does not have to be a complete cut through the full thickness of the fin. It could be an alternate form of weakening the fin to enable a tear to be started readily. For example, the starter line 36 could be a score line only partially through the thickness of the fin, e.g., through one of the two layers of the sheet material that comprise the fin. The score line weakens the fin to enable starting of a tear but is not cut fully through the fin. Further alternate forms of the starter line may include a perforated line, or a combination of perforations, scores and cuts. In any case the starter line defines the pull tab 34 which can be engaged by a user. This allows the user to pull on the fin and use it as a tear strip that removes at least the fin seal 28 from the package and thereby opens the package.

Engagement with the pull tab 34 can be enhanced by forming a first finger hole 38 in the pull tab. Note that that the first finger hole 38 is formed entirely within the fin 20. A second finger hole 40 may be formed in the first end seal 16. Note that a portion 40a of the second finger hole extends onto the fin 20. Providing two finger holes allows the user to engage the fin with one hand and the end seal with the other hand and pull the two pieces apart, which removes the fin seal 28 from the package and lays it open for removal of the catheter.

It will be understood that FIGS. 2-5 show the package 10 somewhat diagrammatically in that the boundaries of the actual body portion 12 do not necessarily have sharply defined edges as the drawings might suggest. Because the body has a three-dimensional shape that merges to flat portions at the end seals 16, 18, the actual transition from one portion of the body to another is somewhat more gradual than implied by the drawings.

Turning now to FIG. 6, a representation of the sheet material 42 is shown prior to any forming steps. The sheet material may be a gas impermeable foil that may be coated with a heat seal layer. It may be a directional tear material, although other materials could be used. To assist in understanding how the sheet material 42 is folded and sealed, the sheet material is shown having longitudinal panels or areas 1-6 which are divided by imaginary demarcation lines A-E. The panels may be designated as side panels 1 and 6, upper panels 2 and 5 and lower panels 3 and 4. The side panels 1 and 6 have longitudinal side edges 44 and 46, respectively. The sheet material 42 of course has top and bottom surfaces, which will become inside and outside surfaces of the package. The inside surfaces are indicated with dotted reference numerals while the outside surfaces will be shown in subsequent figures in solid reference numerals. As mentioned, all or a portion of the inside surfaces may have an adhesive coating or heat seal layer thereon. Typically this is a heat-activated adhesive that will adhere to at least other similarly coated surfaces when pressed against such surfaces and heated. Other types of adhesives could be used.

Also, while FIGS. 6-7 show just a single package, it will be understood that the manufacturing process described below is advantageously performed in a continuous manner. That is, an endless roll of sheet material is fed successively to a series of forming stations, (e.g., stations for wrapping, fin sealing, pinching, end sealing, punching, etc.), with individual packages not being separated from the endless roll until they have passed through all of the stations.

Package formation may begin by unrolling the sheet material into a flat, generally horizontal condition with a front or leading edge 48 that will be fed to successive forming stations or zones. At a loading station a catheter (not shown) is placed on the inside surface of the sheet material 42, at or near the longitudinal center line C of the sheet. The sheet material, with the catheter on its inside surface, is then advanced to a wrapping station or zone wherein the sides of the sheet 42 are wrapped or folded up and around the catheter. The inside surfaces of just the side panels 1 and 6 are placed in confronting relation, with the side edges 44 and 46 brought into or near alignment with one another. This creates the tubular body 12 and the fin 20 of the package.

Next the fin 20 passes through a sealing station where rollers or the like create the fold line 22 and the fin seal 28. Typically the fin seal is created by heated rollers that activate the adhesive on portions of the inside surfaces of side panels 1 and 6. The fin seal portion is indicated in FIG. 7 by the cross-hatched area. This process defines the longitudinal free edge 24 of the fin and the fin seal terminal line 30. In some embodiments it may be desirable to trim the longitudinal free edge 24 of the fin 20 to assure that the side edges of panels 1 and 6 terminate at precisely the same point on the fin. A further alternate embodiment would entail formation of the starter line 36 and finger hole 38 during fin sealing, as explained further below.

FIG. 7 illustrates the package at this stage of its manufacture. Note that at this stage the side panels 1 and 6 are in confronting relation and fold line 22 is formed along demarcation lines A and E. Thus, panels 1 and 6 define the fin 20.

The cross-hatched portions of the inside surfaces of panels 1 and 6 are sealed to one another to define the fin seal 28. The lower portions of the inside surfaces of panels 1 and 6, i.e., the portion between fin seal terminal line 30 and fold line 22, are in confronting relation but they are not sealed to one another; they define the non-sealed portion 32 of the fin 20. The non-sealed portions 32 of panels 1 and 6 may or may not be touching one another, depending on how the body 12 is or is not stretched. But in any event the non-sealed portions of panels 1 and 2 are not adhered to one another.

Also in FIG. 7 note that upper panels 2 and 5 extend from the fold line 22 at demarcation lines A and E. Lower panels 3 and 4 extend from upper panels 2 and 5 at demarcation lines B and D, respectively. Lower panels 3 and 4 are joined at the bottom of the package at demarcation line C. Thus, the package body 12 is formed by panels 2, 3, 4 and 5. These panels are folded generally at the demarcation lines A-E to create the three-dimensional interior cavity 14 in which the catheter resides. Again, the actual package may not have panel boundaries as sharply defined as the figures might suggest.

Once the tubular body 12 and fin 20 have been formed, the next step in the manufacturing process is preparation for creation of the first and second end seals 16 and 18. This is done at a pinching zone where portions of the upper and lower panels of the sheet material are all placed in a generally flat condition, with the upper and lower panels confronting one another. Pinching is done only at selected, spaced locations along the sheet material, leaving intervening sections of panels 2-5 free to form the three-dimensional package body 12. As indicated schematically in FIG. 8, the first end seal 16 of a leading package 10a is formed simultaneously with the immediately-adjacent second end seal 18 of a successive, trailing package 10b. That is, both of the end seals are created at a single pinching and end sealing zone but the single sealing zone creates end seals for what will become separate packages. The leading and trailing packages 10a and 10b are subsequently separated from one another at a final severing station. In the pinching zone, portions of the body panels 2, 3, 4 and 5 are pinched together into a generally horizontal condition. In those portions of the sheet that are pinched, the inside surfaces of panels 2 and 3 are placed in contact with one another, as are the inside surfaces of panels 4 and 5. Also, in connection with the pinching operation the fin 20 is folded down into a generally horizontal condition. Folding of the fin may be done either before, during or after the pinching operation of panels 2-5.

Once pinching and folding operations are complete, the sheet enters the end seal station. Here hot, transverse rollers contact the pinched portions to form the first end seal 16 of a leading package and the second end seal 18 of a trailing package. The end seals 16, 18 are shown in FIG. 8 by the cross-hatching that is in a different direction from that of the fin seal 28. Note that the end sealing rollers will also cross over the folded-down fin 20, resulting in: a) a double-sealed area 50 (as indicated at the double cross-hatched areas) of the fin panels 1 and 6 at the area of the fin seal 28; and b) a single-sealed area 52 (as indicated at the single cross-hatched area of the fin) of the fin panels 1 and 6 between the fold line 22 and the fin seal terminal line 30. Prior to forming the end seals this single-sealed area 52 was part of the non-sealed portion of the fin. The single-sealed area of the fin is shown at 52 and exists only at the area of the end seals 16 and 18.

It is pointed out that since the outside surfaces of the sheet panels 1, 2, 5 and 6 do not have an adhesive on them, the end sealing operation does not result in fastening the fin to the outside surface of either upper panel. In the embodiment illustrated in FIG. 8 the fin 20 is folded onto upper panel 5 but the fin will not stick to that panel. After end sealing the fin 20 is free to fold back up, out of the plane of the end seals, as shown by FIG. 1.

While the package is held taught during the end sealing operation, it is an advantageous time to perform the slitting and punching operations needed to form the starter line 36 and the first finger hole 38, if this was not already done during fin seal formation. The second finger hole 40 can also be formed at this time. In this regard, it will be noted that the second finger hole 40 can be formed by a simple punching operation that extends through both the first end seal 16 and the folded-down fin 20. However, formation of the starter line 36 and first finger hole 38 requires a more delicate operation because these are formed only in the fin 20. That is, the starter line 36 impacts one or both of the panels 1 and 6 only and the first finger hole 38 impacts both panels 1 and 6 only. In other words, none of panels 2-5 bear any portion of starter line 36 or finger hole 38. The starter line 36 and finger hole 38 can be formed by laser cutting or by a vertical, mechanical punch while the material is taught and being passed through the fin sealing rollers. Preferably the starter line will extend to the single-sealed area 52 of the fin 20. Terminating the starter line in the single-sealed area 52 provides a good compromise between maintaining the integrity of the package seal during shipping and handling and minimizing the opening force required when it is time to open the package.

The final step in the manufacturing process is severing the finished, leading package off the front end of the sheet material. The severing action separates the first end seal 16 of the leading package from the second end seal 18 of a trailing package. It also defines the end free edge 26 of the fin. Severing leaves a finished package 10 in the condition generally shown in FIG. 1.

The use of the package may proceed as follows. A user will engage the package 10 in two places, the pull tab 34 (via the first finger hole 38) and the first end seal 16 (via the second finger hole 40). The user will then pull these two portions apart. As this is done the starter line 36 will direct the initial separation or tear of the two components such that a tear line propagates toward the non-sealed portion 32 of the fin 28. Because, at least in part, of the extra strength afforded by the double thickness of the fin seal 28, the tear line will not propagate onto or through the fin seal, but instead the tear line will propagate through the single thicknesses of either the non-sealed portion 32, in panels 1 and 6, or possibly along the fold line 22 or the other side of the fold line 22, in panels 2 and 5, or some combination of these. In any event, all or most of the fin seal 28 between the end seals 16 and 18 may be removed, laying open the package body 12 as only non-sealed panels of the package body remain. Packages of the type described herein, with a fin seal used to tear open the package, result in a clean, straight tear. Using the fin seal for opening will also allow the package to be opened on the top and leave the opened package lying flat for easy removal of the catheter by the user. This contrasts with present packages that open the package on its side. Furthermore, a lower package opening force is required to open along the fin seal, compared to known opening features.

It should be understood that various changes and modifications to the presently preferred embodiments described herein will be apparent to those skilled in the art. Such changes and modification can be made without departing from the spirit and scope of the invention disclosed herein.

For example, the arrangement of the starter line and finger holes could be other than as shown. The starter line 36 could extend from the end free edge 26 of the fin instead of from the longitudinal free edge 24 as shown. This may allow moving the second finger hole 40 off of the fin entirely so as to not interfere with a propagating tear line upon opening. A starter line beginning at the end free edge 26 might also benefit from deletion of the first finger hole. In this case the fin itself may serve as the pull tab. In another alternate embodiment the starter line could be formed in the fin, extending from the longitudinal free edge at a point remote from either end seal. Such a starter line could also have a first finger hole placed nearby and/or have the second finger hole placed in the fin at the nearest end seal.

The invention claimed is:

1. A package, comprising a sheet material having first and second side panels and upper and lower panels, the sheet material being wrapped into a three-dimensional configuration wherein the first and second side panels are placed in confronting relation to define a fin having a longitudinal free edge and opposed end free edges, at least a portion of the side panels parallel to the longitudinal free edge of the fin being adhered to one another to define a fin seal extending between the longitudinal free edge and a terminal line parallel to the longitudinal free edge, portions of the upper and lower panels being placed in confronting relation and said portions of the upper and lower panels being adhered to one another to define first and second end seals, and a starter line formed in the fin at a location intermediate the end free edges extending from the longitudinal free edge of the fin toward the upper panels wherein the starter line directs tearing of the package parallel to the longitudinal free edge.

2. The package of claim 1 further comprising a first finger hole formed in the fin.

3. The package of claim 2 further comprising a second finger hole formed in one of the end seals extending onto the fin.

4. The package of claim 1 wherein at least a portion of the side panels of the fin are not adhered to one another to define a non-sealed portion of the fin, and wherein one of the first and second end seals extends onto the non-sealed portion of the fin to define a single-sealed area of the fin, the starter line extending from the free edge of the fin to the single-sealed area.

5. The package of claim 1 wherein the fin is connected to the upper panels at a fold line.

6. The package of claim 5 wherein the fin seal extends from the free edge of the fin to a fin seal terminal line that is spaced from the fold line, with the space between the fold line and the fin seal terminal line defining a non-sealed portion of the fin, and wherein one of the first and second end seals extends onto the non-sealed portion of the fin to define a single-sealed area of the fin, the starter line extending from the free edge of the fin to the single-sealed area.

7. The package of claim 6 wherein the starter line extends to about a quarter inch from the fold line.

8. The package of claim 7 wherein the portion of the starter line closest to the fold line extends within about 15 to about 20 degrees of parallel to the fold line.

9. The package of claim 2 wherein the starter line defines an arc which is concentric with the first finger hole.

10. A package, comprising:
an elongated sheet having first and second side panels, the sheet being wrapped into a three-dimensional configuration wherein the side panels are in confronting relation to one another to define a fin having a longitudinal free edge and opposed end free edges;
at least a portion of the fin having the first and second side panels parallel to the longitudinal free edge sealed to one another to define a fin seal that extends between the longitudinal free edge and a fin seal terminal line parallel to the longitudinal free edge; and
a starter line formed in the fin at a location intermediate the end free edges extending from the longitudinal free edge of the fin to define a pull tab which can be engaged by a user to pull on the fin and separate at least a portion of the fin from the package and thereby open the package wherein the starter line directs tearing of the package parallel to the longitudinal free edge.

11. The package of claim 10 wherein the elongated sheet further comprises upper and lower panels, portions of the upper and lower panels being placed in confronting relation and said portions of the upper and lower panels being adhered to one another to define first and second end seals.

12. The package of claim 11 further comprising a first finger hole formed in the fin.

13. The package of claim 12 further comprising a second finger hole formed in one of the end seals extending onto the fin.

14. The package of claim 11 wherein at least a portion of the side panels of the fin are not adhered to one another to define a non-sealed portion of the fin, and wherein one of the first and second end seals extends onto the non-sealed portion of the fin to define a single-sealed area of the fin, the starter line extending from the free edge of the fin to the single-sealed area.

15. The package of claim 11 wherein the fin is connected to the upper panels at a fold line.

16. The package of claim 15 wherein the fin seal extends from the free edge of the fin to a fin seal terminal line that is spaced from the fold line, with the space between the fold line and the fin seal terminal line defining a non-sealed portion of the fin, and wherein one of the first and second end seals extends onto the non-sealed portion of the fin to define a single-sealed area of the fin, the starter line extending from the free edge of the fin to the single-sealed area.

17. The package of claim 16 wherein the starter line extends to about a quarter inch from the fold line.

18. The package of claim 17 wherein the portion of the starter line closest to the fold line extends within about 15 to about 20 degrees of parallel to the fold line.

19. The package of claim 12 wherein the starter line defines an arc which is concentric with the first finger hole.

20. A package, comprising:
an elongated sheet having first and second side panels, the sheet being wrapped into a three-dimensional configuration wherein at least portions of the side panels overlap one another, at least a first portion of the overlapping side panels parallel to a longitudinal free edge being adhered to one another to define a fin seal having a longitudinal free edge and opposed end free edges and extending between the longitudinal free edge and a terminal line parallel to the longitudinal free edge, at least a second portion of the overlapping side panels remote from said fin seal being adhered to one another to define a single-sealed area; and
a starter line formed in the fin seal at a location intermediate the end free edges extending from the longitudinal free edge of the fin seal to the single-sealed area wherein the starter line directs tearing of the package parallel to the longitudinal free edge.

21. The package of claim 20 wherein the elongated sheet further comprises upper and lower panels, portions of the upper and lower panels being placed in confronting relation and said portions of the upper and lower panels being adhered to one another to define first and second end seals.

22. The package of claim 21 further comprising a first finger hole formed in the fin seal.

23. The package of claim 22 further comprising a second finger hole formed in one of the end seals extending onto the fin.

24. The package of claim 21 wherein at least a portion of the overlapping side panels are not adhered to one another to define a non-sealed portion, and wherein one of the first and second end seals extends onto the non-sealed portion to define said single-sealed area.

25. The package of claim 21 wherein overlapping portions of the side panels are connected to the upper panels at a fold line.

26. The package of claim 25 wherein the fin seal extends from the free edge to a fin seal terminal line that is spaced from the fold line, with the space between the fold line and the fin seal terminal line defining a non-sealed portion, and wherein one of the first and second end seals extends onto the non-sealed portion to define said single-sealed area of the fin, the starter line extending from the free edge to the single-sealed area.

27. The package of claim 26 wherein the starter line extends to about a quarter inch from the fold line.

28. The package of claim 27 wherein the portion of the starter line closest to the fold line extends within about 15 to about 20 degrees of parallel to the fold line.

29. The package of claim 22 wherein the starter line defines an arc which is concentric with the first finger hole.

* * * * *